(12) United States Patent
Bedell et al.

(10) Patent No.: US 9,739,728 B1
(45) Date of Patent: Aug. 22, 2017

(54) AUTOMATIC DEFECT DETECTION AND CLASSIFICATION FOR HIGH THROUGHPUT ELECTRON CHANNELING CONTRAST IMAGING

(71) Applicant: International Business Machines Corporation, Armonk, NY (US)

(72) Inventors: Stephen W. Bedell, Wappingers Falls, NY (US); Renee T. Mo, Yorktown Heights, NY (US); Kunal Mukherjee, White Plains, NY (US); John A. Ott, Greenwood Lake, NY (US); Devendra K. Sadana, Pleasantville, NY (US); Brent A. Wacaser, Putnam Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/187,467

(22) Filed: Jun. 20, 2016

(51) Int. Cl.
*G01N 23/207* (2006.01)
*G06K 9/46* (2006.01)

(52) U.S. Cl.
CPC ......... *G01N 23/207* (2013.01); *G06K 9/4671* (2013.01); *G01N 2223/401* (2013.01)

(58) Field of Classification Search
USPC ........................................ 250/307, 306, 310
See application file for complete search history.

(56) References Cited

U.S. PATENT DOCUMENTS

| 5,589,690 A | * | 12/1996 | Siewert | ............... | G01N 23/207 |
| | | | | | 250/390.06 |
| 6,711,293 B1 | | 3/2004 | Lowe | | |
| 2007/0254154 A1 | * | 11/2007 | Wong | .................... | B82Y 30/00 |
| | | | | | 428/402 |

* cited by examiner

*Primary Examiner* — Kiet T Nguyen
(74) *Attorney, Agent, or Firm* — Scully, Scott, Murphy & Presser, P.C.; Louis J. Percello, Esq.

(57) ABSTRACT

Imaging and processing techniques are employed to identify crystalline defects obtained by ECCI from surrounding topography and is combined with defect counting and automatic classification.

19 Claims, 5 Drawing Sheets

FIG. 4A
Type 1

FIG. 4B
Type 2

FIG. 4C
Type 3

FIG. 4D
Type 4

Intensity (a.u.)

Distance (a.u.)

AUTOMATIC DEFECT DETECTION AND CLASSIFICATION FOR HIGH THROUGHPUT ELECTRON CHANNELING CONTRAST IMAGING

BACKGROUND

The present application relates to electron channeling contrast imaging (ECCI) of a crystalline material. More particularly, the present application relates to a method that employs image recognition and processing techniques to identify defects obtained by ECCI of a crystalline material for automatic characterization.

In the manufacturing of microelectronics, defects in the crystalline quality of the material can adversely affect the material quality. As materials (such as, Ge, SiGe and/or III-V compound semiconductors) are added into the manufacturing line, defects caused by the epitaxy and processing of dissimilar materials are more abundant than with silicon only technologies. Therefore, it is important to test the defect density and other properties in the materials to control the growth and processing in the line.

Most of the conventional techniques used for such defect detection such as, for example, TEM, are destructive, since they require cutting, polishing and/or thinning of the sample being tested. Although there are some non-destructive techniques for defect detection, such techniques are limited. For example, known non-destructive techniques such as, for example, electron channeling contrast imaging (ECCI), have low throughput, which hinders the ability of the known non-destructive techniques for providing accurate and efficient defect detection.

In view of the above, there is a need for providing a way to use ECCI for in-line microelectronics metrology of crystalline defects for crystalline semiconductor materials such as, for example, germanium (Ge), silicon germanium alloys (SiGe), or III-V compound semiconductors.

SUMMARY

Image recognition and processing techniques are employed to identify crystalline defects obtained by ECCI for automatic classification.

In one aspect of the present application, a method for automatic detection and classification of crystalline defects of a crystalline material is provided. In one embodiment of the present application, the method includes obtaining a first image of a crystalline material utilizing electron channeling contrast imaging (ECCI). The ECCI conditions are then altered to obtain a second image. Next, the crystalline defects of the second image are distinguished from other features present in the crystalline material, and thereafter the number of the crystalline defects is tallied. Features of the crystalline defects in the second image are then processed, using an algorithm, to determine a defect fingerprint for each of the crystalline defects. Next, the defect type of each of the crystalline defects is classified by comparing the fingerprint to a library containing images of defect fingerprints of known defect types.

In some embodiments of the present application, the method may further include tallying and storing the number of each type of crystalline defect and the total area scanned, and determining the number of each type of crystalline defects per unit area of the crystalline material.

In another embodiment of the present application, a method for automatic detection of crystalline defects of a crystalline material is provided. In one embodiment of the present application, this method may include providing a substrate containing a plurality of patterned structures comprising a crystalline material, wherein each of the patterned structure is misaligned relative to at least one type of crystalline defect present in each patterned structure, and obtaining an image of each patterned structure utilizing electron channeling contrast imaging (ECCI).

DETAILED DESCRIPTION

The present application will now be described in greater detail by referring to the following discussion and drawings that accompany the present application. It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that the various embodiments of the present application may be practiced without these specific details. In other instances, well-known structures or processing steps have not been described in detail in order to avoid obscuring the present application.

Electron channeling contrast imaging (ECCI) is a non-destructive advanced SEM-based technique that can be used to characterize crystalline defects, offering advantages of destructive techniques. Unlike particle/contamination related defects, there are a limited number of crystallographic defects that need to be classified. Notably, the crystallographic defects that need to be classified include dislocations (misfit and threading), stacking faults and micro-twins. It would be very beneficial for an in-line ECCI tester to automatically classify defects; currently, ECCI signals are not automatically classified.

Moreover, ECCI is limited by topography. Thus, imaging processing is a must for small features.

Figure 1:
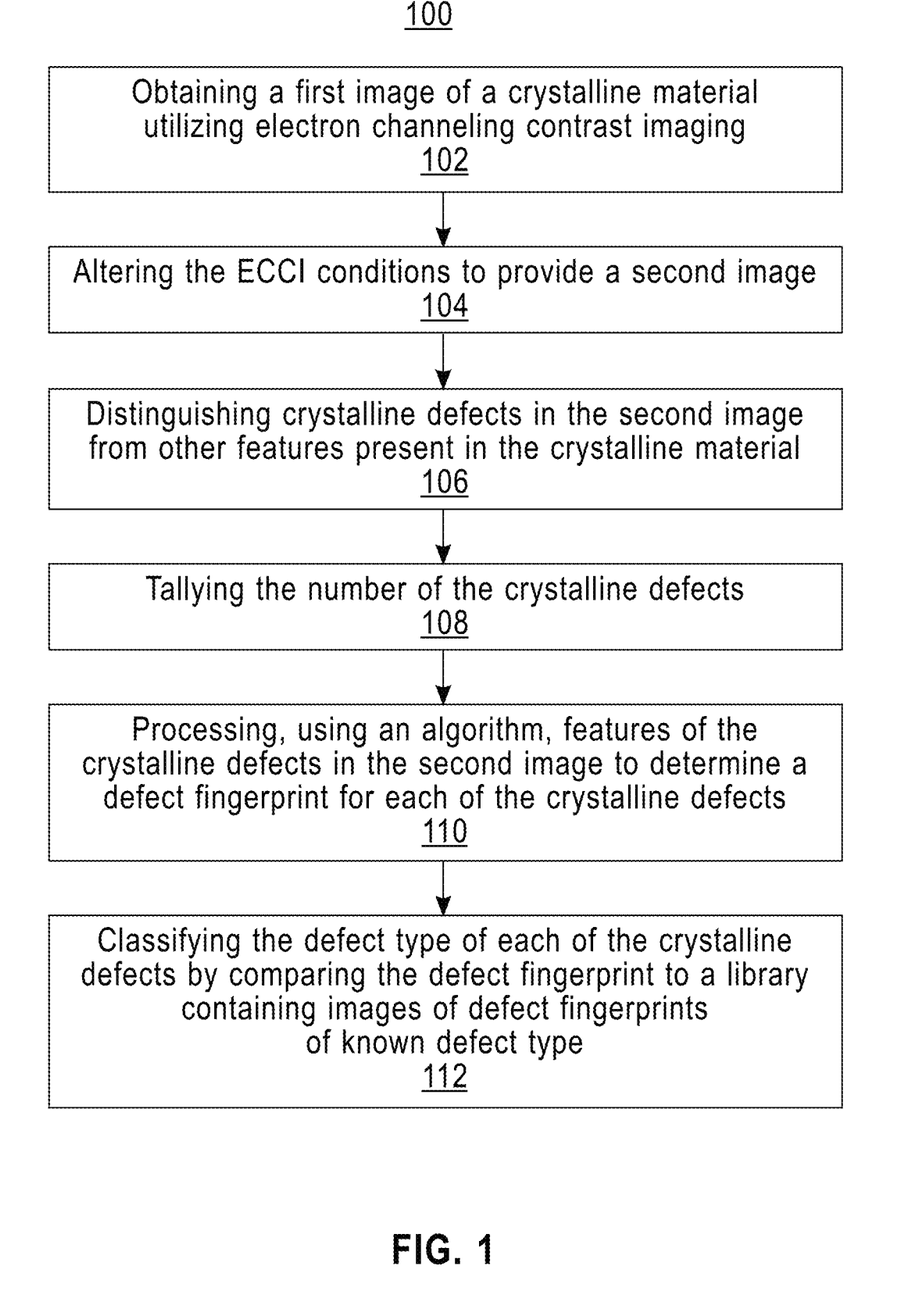
FIG. 1 is a flow diagram illustrating the basic processing steps that can be employed in one embodiment of the present application.

Reference is first made to FIG. 1 which represents a flow diagram 100 illustrating the basic processing steps that can be employed in one embodiment of the present application. Notably, FIG. 1 depicts a method for automatic detection and classification of crystalline defects of a crystalline material. The flow diagram 100 of FIG. 1 includes a step 102 of obtaining a first image of a crystalline material utilizing electron channeling contrast imaging (ECCI). The ECCI conditions are then altered in step 104 to provide a second image. Next and in step 106, crystalline defects are distinguished from other features present in the second image. In step 108, the number of the crystalline defects is then tallied. Features of the crystalline defects in the second image are then processed, using an algorithm in step 110, to determine a defect fingerprint for each of the crystalline defects. Next and in step 112, the defect type of each of the crystalline defects is classified by comparing the fingerprint to a library containing images of defect fingerprints of known defect types.

The method of the present application may begin by first providing a crystalline material for ECCI. The crystalline material may be an unpatterned layer or a patterned layer that is present on a surface of a substrate. The substrate may include any semiconductor material having semiconductor properties. Examples of semiconductor materials that can be used as the substrate include, but are not limited to, silicon (Si), germanium (Ge), silicon germanium alloys (SiGe), silicon carbide (SiC), III-V compound semiconductors or II-VI compound semiconductors. Collectively, the substrate and crystalline material may be referred to as a semiconductor structure or sample that can be imaged by ECCI.

In some embodiments, the substrate may be a bulk semiconductor substrate. The term "bulk" denotes the entirety of the semiconductor substrate is composed of at least one semiconductor material with no insulators and/or conductive materials present therein.

In yet other embodiments of the present application, the substrate may be a semiconductor-on-insulator (SOI) including, from bottom to top, a handle substrate, an insulator layer and a topmost semiconductor layer. In some embodiments, the handle substrate may be composed of one of the semiconductor materials mentioned above. In other embodiments, the handle substrate may be composed of a dielectric material or a conductive material. In yet other embodiments, the handle substrate may be omitted. The insulator layer of the SOI substrate may be composed of a dielectric oxide, dielectric nitride or a multilayered stack thereof. In one example, the insulator layer of the SOI substrate may be composed of silicon dioxide and/or silicon nitride. The topmost semiconductor layer of the SOI substrate may be composed of one of the semiconductor materials mentioned above. The SOI can be formed utilizing well known processes including, for example, a layer transfer process, or by a SIMOX (separation by ion implantation of oxygen) process.

The semiconductor material that provides the substrate may have any of the well known crystal orientations, including, for example, {100}, {110}, or {111}. In some embodiments of the present application, at least an upper portion of the semiconductor material that provides the substrate is a single crystalline semiconductor material.

In some embodiments, the substrate may include a blanket layer of crystalline material located thereon. In some embodiments, the substrate may include a plurality of patterned structures located thereon. In yet another embodiment, the crystalline material (unpatterned or patterned) may represent a topmost crystalline semiconductor material portion of substrate.

In some embodiments of the present application, the crystalline material may be a semiconductor material including one of the semiconductor materials mentioned above for substrate. In some embodiments of the present application, the semiconductor material that provides the crystalline material is different from the semiconductor material of the substrate. In one example, the crystalline material is composed of a silicon germanium alloy or a III-V compound semiconductor, while the substrate is composed of silicon.

In some embodiments of the present application, the crystalline material can be formed by epitaxially growth (or deposition). In the case of the patterned structures containing the crystalline material, a patterning process may follow the epitaxial growth of the crystalline material.

The terms "epitaxial growth and/or deposition" and "epitaxially formed and/or grown" mean the growth of a material on a deposition surface of a material, in which the material being grown has the same crystalline characteristics as the material of the deposition surface. In an epitaxial deposition process, the chemical reactants provided by the source gases are controlled and the system parameters are set so that the depositing atoms arrive at the deposition surface of a material with sufficient energy to move around on the surface and orient themselves to the crystal arrangement of the atoms of the deposition surface. Therefore, an epitaxial material that is formed by an epitaxial deposition process has the same crystalline characteristics as the deposition surface on which it is formed. For example, an epitaxial semiconductor material deposited on a {100} crystal surface will take on a {100} orientation. Examples of various epitaxial growth processes that are suitable for use in forming the silicon germanium alloy layer 14L include, e.g., rapid thermal chemical vapor deposition (RTCVD), low-energy plasma deposition (LEPD), ultra-high vacuum chemical vapor deposition (UHVCVD), atmospheric pressure chemical vapor deposition (APCVD), molecular beam epitaxy (MBE) or metal-organic CVD (MOCVD). The temperature for epitaxial deposition typically ranges from 250° C. to 900° C.

A number of different source gases may be used for the deposition of crystalline material. Carrier gases like hydrogen, nitrogen, helium and argon can be used. The epitaxially grown material can be formed is from 2 nm to 200 nm. Other thicknesses that are lesser than, or greater than, the aforementioned thickness range can also be employed in the present application.

In one embodiment, the patterning of the epitaxially grown crystalline material used to provide the patterned structures may include lithography and etching. Lithography includes forming a photoresist material (not shown) on the topmost surface of the epitaxally grown crystalline material. The photoresist material can be formed utilizing a deposition process such as, for example, spin-on coating, evaporation, or chemical vapor deposition. Following the deposition of the photoresist material, the photoresist material is exposed to a pattern of irradiation, and thereafter the exposed resist material is developed utilizing a conventional resist developer to provide a patterned photoresist material. At least one etch such as, for example, a reactive ion etch, can be used to complete the pattern transfer. Following at least one pattern transfer etch process, the patterned photoresist material can be removed from the structure utilizing a conventional resist stripping process such as, for example, ashing.

In another embodiment, the patterning of the epitaxially grown crystalline material used to provide the patterned structures may include a sidewall image transfer (SIT) process. In a typical SIT process, spacers are formed on sidewalls of a sacrificial mandrel. The sacrificial mandrel is removed and the remaining spacers are used as a etch mask. The spacers are then removed after etching.

In yet another embodiment, the patterning of the epitaxially grown crystalline material used to provide the patterned structures may include a direct self-assembly (DSA) process. DSA uses block copolymers that can phase separate during an anneal process. Each first phase separate block can then be removed, while maintaining second phase separated blocks as an etch mask.

In some embodiments of the present application, each patterned structure comprises a fin structure. As used herein, a "fin" is a structure that has a first pair of sidewalls along a lengthwise direction that is longer than a second pair of sidewalls along a widthwise direction.

Figure 2:
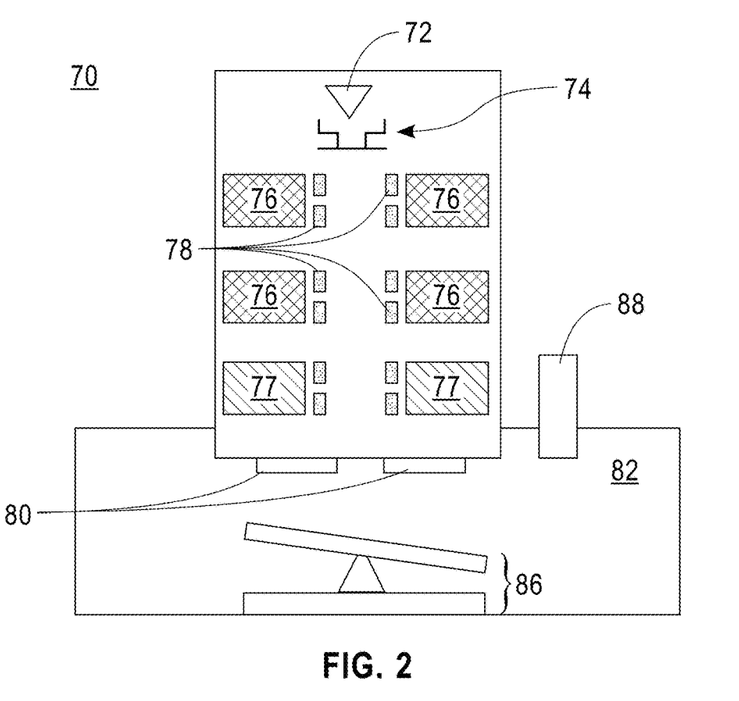
FIG. 2 is a schematic of an ECCI apparatus that can be used in the present application.

After providing the semiconductor structure containing a crystalline material, the semiconductor structure is placed on a surface of a sample holder within a sample chamber of an apparatus that is capable of performing ECCI. One such apparatus is shown in FIG. 2. Notably, FIG. 2 shows an apparatus 70 which may be employed in the present application for ECCI of a crystalline material such as described above. The apparatus 70 contains an electron source 72 located within a probe. The probe also includes electrostatic lens 74, a plurality of condenser lenses 76, objective lenses 77 and deflection coils 78. Detectors 80 are located at the end of the probe. In some embodiments, detectors 80 may be electron backscattering detectors. The apparatus 70 further includes a sample chamber 82 and a sample holder 86 that may be tilted as shown. Another detector 88, may also be present. In some embodiments, detector 88 may be a secondary detector. The apparatus 70 shown in FIG. 2 and the conditions that are required to use the same are well known to those skilled in the art.

After placement of the semiconductor structure on a surface of a sample holder within a sample chamber of an apparatus that is capable of performing ECCI, an alignment step is typically performed so as to aligned the probe and the semiconductor structure. Typically, alignment is performed manually utilizing techniques well known to those skilled in the art. For example, the apparatus that can be used for ECCI contains various adjustment knobs and fine adjustment knobs that can be manually adjusted so as to obtain proper alignment of the probe and the semiconductor structure. Also, alignment adjustment may be achieved by varying the tilt of the sample holder containing the semiconductor structure.

Figure 3A:
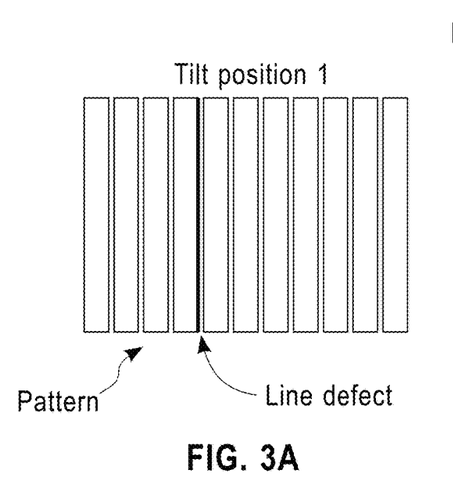
FIG. 3A is an image of a crystalline material obtained by ECCI at a first tilt angle.

After the alignment process and as described in step 102, an image of the semiconductor structure including the crystalline material is obtained by ECCI. The ECCI conditions that are employed to obtain the image are well known to those skilled in the art. In one example, the conditions for ECCI include using a 20 kV accelerating voltage, a high probe current of 4 nA, a backscatter electron detector, and the sample (i.e., the semiconductor structure containing the substrate and crystalline material) tilted to a 220 channeling condition. The sample to pole-piece distance is 5 mm. FIG. 3A of the present application shows an exemplary image of a semiconductor structure including a crystalline material that was obtained by ECCI using a first tilt angle.

Figure 3B:
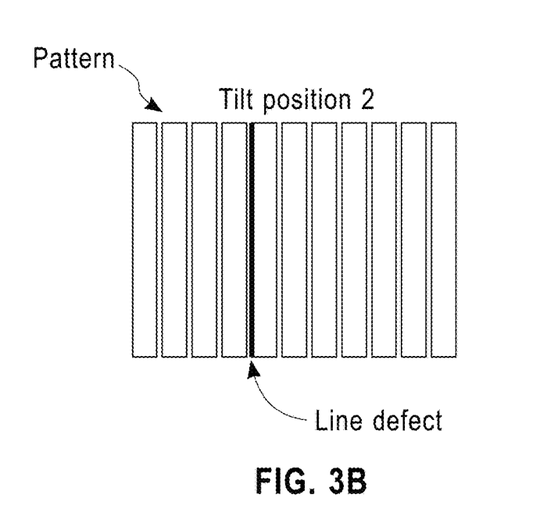
FIG. 3B is an image of a crystalline material obtained by ECCI at a second tilt angle.
Figure 4A:
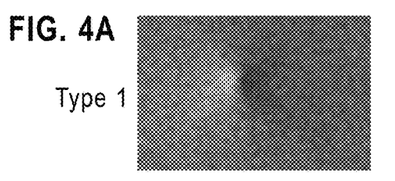
FIGS. 4A-4D are images showing the features of various types of defects present in a crystalline material.
Figure 4B:
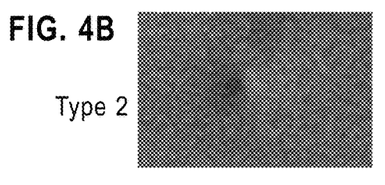
Figure 4C:
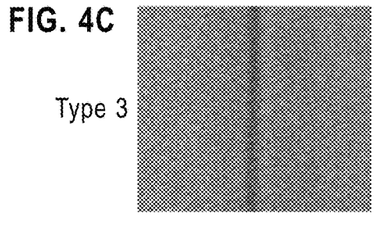
Figure 4D:
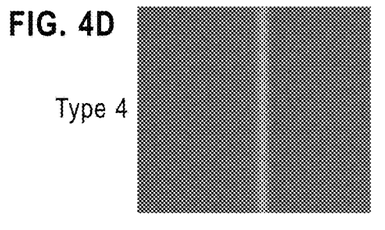
Figure 5A:
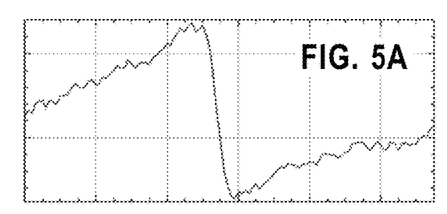
FIGS. 5A-5D are the defect fingerprints for each of the crystalline defects shown in FIGS. 5A-5D.
Figure 5B:
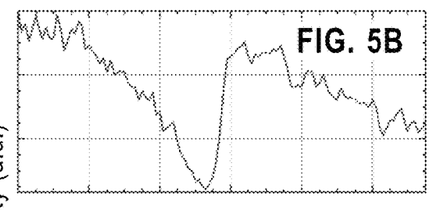
Figure 5C:
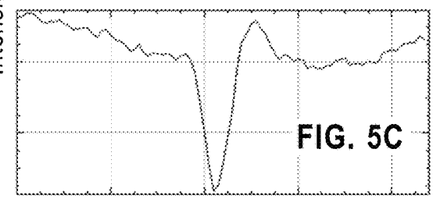
Figure 5D:
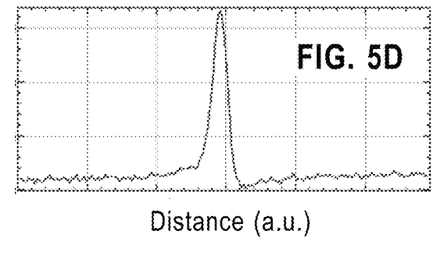

Next, and as shown in step 104, the ECCI conditions are altered to provide a second image. FIG. 3B of the present application shows an exemplary image of a semiconductor structure including a crystalline material that was obtained by adjusting the ECCI conditions to a second tilt angle that is different from the first tilt angle.

In one embodiment of the present application, the alteration may include adjusting the tilt of the semiconductor structure including the crystalline material in small increments of less than 0.1 degrees. Titling may be achieved in the present application, by adjusting the tilt of the sample holder 86. In some embodiments, the adjusting of the tilt of the sample holder 86 containing the semiconductor structure can be performed manually.

In another embodiment of the present application, the alteration may include adjusting the accelerating voltage of the electron beam so as to modify the optimum channeling conditions. Such a change in the accelerating voltage will void the channeling condition from being satisfied, reducing the defect contrast.

In another embodiment of the present application, the alteration may include tilting the sample to the complementary channeling condition (negative g-vector) as that used for the first image. This will change the visual appearance of the defect more strongly than it will of non-crystalline defects or intentional substrate topographical features. For example, the second image can be obtained at −220 channeling, if the first image is obtained at 220 channeling condition.

In another embodiment of the present application, the alteration may include changing the detector configuration to collect different kinds of complementary signal. In one example, the alteration may include switching the detector from backscatter to secondary electron.

Next, and in step 106, crystalline defects are distinguished from other features present in the second image. The distinguishing the crystalline defects may be performed by comparing the first and second images to each other.

Next, and in step 108, the number of the crystalline defects is then tallied. The tallying of the number of defects may be performed manually by counting each crystalline defect observed in the image. Alternatively, the tallying may be performed utilizing well known software that is capable of performing the same.

The features of the crystalline defects in the second image are then processed, using an algorithm in step 110, to determine a defect fingerprint for each of the crystalline defects. FIGS. 4A-4D are images showing the features of the various types of defects present in a crystalline material that can be obtained in step 106 of the present application. FIGS. 5A-5D are graphs showing the defect fingerprints for each type of defect that can be obtained in step 110 of the present application.

In one embodiment of the present application, the processing may include generating a line profile fingerprint of an extended crystalline defect such as a misfit dislocation or stacking fault. A line profile may be obtained by plotting the grayscale value orthogonal to the line defect. Such a line profile can also be obtained by averaging the grayscale values parallel to the line defect before moving orthogonally to reduce noise. In the case of threading dislocations, the line profile is obtained along the direction of steepest descent in the grayscale value. Information about each crystalline defects can also be stored in two-dimensional image form in addition to the line profile. This can be achieved using image cropping and saving the image in the computer memory.

Next and in step 112, the defect type of each of the crystalline defects is classified by comparing the fingerprint to a library containing images of defect fingerprints of known defect types. The library can comprise of line profiles as well as two-dimensional images. The classification may be performed utilizing well known computer software and algorithms that are capable of performing such classification. Comparison of line profiles can be achieved by subtraction of the obtained line profiles with that of references. Comparison of two-dimensional images can be performed using image comparison algorithms such as histogram matching or scale-invariant feature transform (SIFT). One such image matching technique is disclosed, for example, in U.S. Pat. No. 6,711,293, the entire content of which is incorporated by reference.

In some embodiments of the present application, the method of the present application may further include a step of tallying and storing the number of each type of crystalline defect and the total area scanned; and determining the number of each type of crystalline defects per unit area of the crystalline material. The tallying of each type of crystalline defect may be performed manually or by a computer or processor, and the storing the number of the number of types of crystalline defects may be performed using a computer of processor. In one embodiment of the present application, the tallying may include counting a number of frames with the specific type of crystalline defect and without the specific type of crystalline defect. Such tallying may be performed for each type of crystalline defect present in the crystalline material.

The determining the number of each type of crystalline defects per unit area of the crystalline material can be performed manually or by utilizing a computer program embodied within a computer or processor.

In another aspect of the present application, a method for umambigous detection of crystalline defects of a crystalline material is provided. This method may include providing a substrate containing a plurality of patterned structures comprising a crystalline material, wherein each of the patterned structure is misaligned relative to at least one type of extended crystalline defect such as a misfit dislocation present in each patterned structure, and obtaining an image of each patterned structure utilizing electron channeling contrast imaging (ECCI). Processing steps 104-112 of FIG. 1 and the steps of tallying and storing the number of each type of crystalline defect and the total area scanned; and determining the number of each type of crystalline defects per unit area of the crystalline material may then be performed.

Figure 6A:
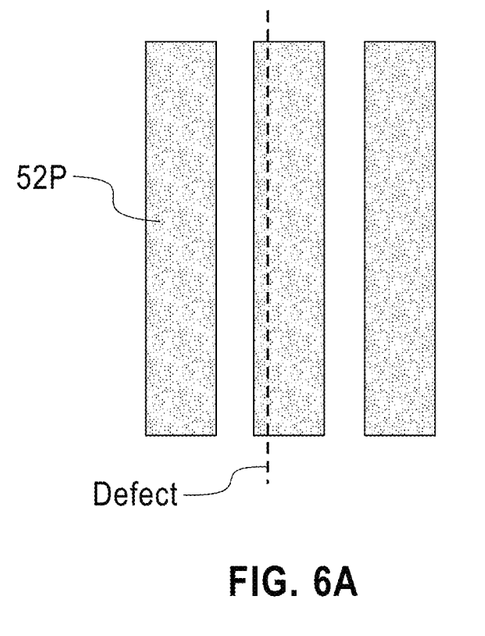
FIG. 6A is a schematic of a prior art structure including a plurality of semiconductor fins in which the edges of the semiconductor fins are aligned with the direction of the defects.
Figure 6B:
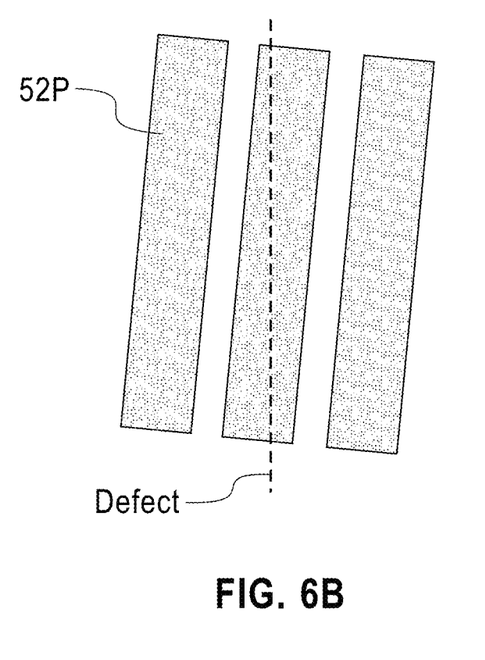
FIG. 6B is a schematic of a structure of the present application including a plurality of semiconductor fins in which each semiconductor fins is tilted so as to be misaligned relative to the direction of the defects.

Reference is first made to FIG. 6A, which illustrates a prior art structure including a plurality of semiconductor fins 52P in which the edges of the semiconductor fins 52P are aligned with the direction of the defects. In such a structure, it is difficult for an in-line ECCI operator to distinguish between the defects and the edges of the fins. To circumvent this problem, the structure of FIG. 6B is provided and is used in ECCI. Notably, FIG. 6B is a schematic of a structure of the present application including a plurality of semiconductor fins 52P in which each semiconductor fin is tilted so as to be misaligned relative to the direction of the defects. In such a structure, it is easy for an in-line ECCI operator to distinguish between the defects and the edges of the fins.

Figure 7:
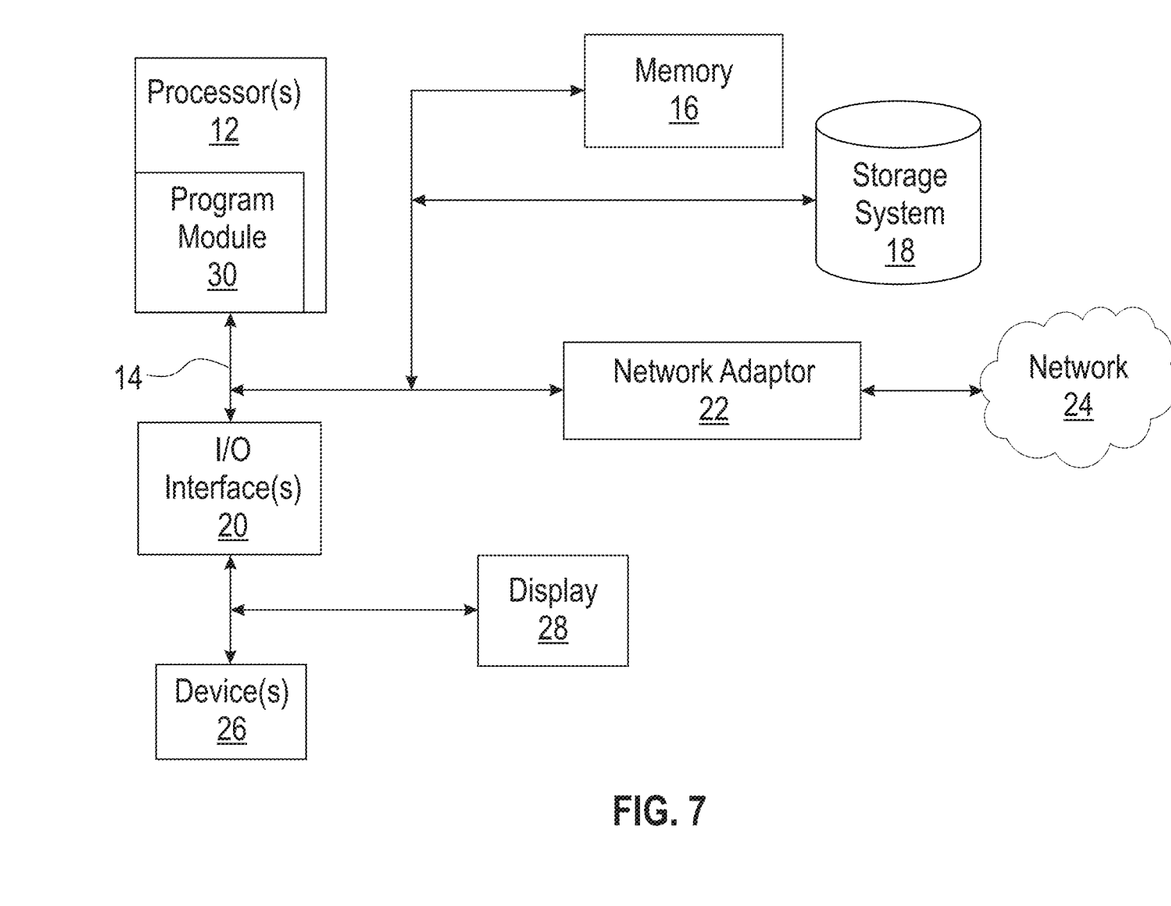
FIG. 7 is a schematic of an exemplary computer or processing system that may be used in the present application.

FIG. 7 is a schematic of an example computer or processing system that may be used in concert with an ECCI apparatus such as, apparatus 70 of FIG. 2 and can perform some of the processing steps such as, for example, processing steps 106, 108, 110 and 112 mentioned above. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 7 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a program module 30 that performs the calculating and interpolating described herein. The program module 30 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

The computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

Some aspects of the present application may be a system, a method, and/or a computer program product. The computer program product may include a computer readable storage medium (or media) having computer readable program instructions thereon for causing a processor to carry out aspects of the present application.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present application may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present application.

Some aspects of the present application are described herein with reference to flowchart illustrations and/or block diagrams of methods, apparatus (systems), and computer program products according to embodiments of the application. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the drawings illustrate the architecture, functionality, and operation of possible implementations of systems, methods, and computer program products according to various embodiments of the present application. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the present application has been particularly shown and described with respect to preferred embodiments thereof, it will be understood by those skilled in the art that the foregoing and other changes in forms and details may be made without departing from the spirit and scope of the present application. It is therefore intended that the present application not be limited to the exact forms and details described and illustrated, but fall within the scope of the appended claims.

What is claimed is:

1. A method for automatic detection and classification of crystalline defects of a crystalline material, said method comprising:
   obtaining a first image of a crystalline material utilizing electron channeling contrast imaging (ECCI) under a particular channeling condition;
   altering the ECCI conditions to obtain a second image;
   distinguishing crystalline defects from other features present in said second image;
   tallying the number of said crystalline defects;
   processing, using an algorithm, features of said crystalline defects in said second image to determine a defect fingerprint for each of said crystalline defects; and
   classifying the defect type of each of said crystalline defects by comparing said defect fingerprint to a library containing images of defect fingerprints of known defect types.

2. The method of claim 1, wherein said altering said ECCI conditions comprises tilting said crystalline material.

3. The method of claim 1, wherein said altering said ECCI conditions comprises tilting said crystalline material to a complementary channeling condition.

4. The method of claim 1, wherein said altering said ECCI conditions comprises changing the accelerating voltage of an electron beam, modifying the optimum channeling conditions.

5. The method of claim 1, wherein said altering said ECCI conditions comprises changing a detector configuration to collect different finds of complementary signal.

6. The method of claim 1, wherein said processing comprises generating a line profile and two-dimensional cropped images of said crystalline defect.

7. The method of claim 1, further comprising:
   tallying and storing the number of each type of crystalline defect and the total area scanned; and
   determining the number of each type of crystalline defects per unit area of said crystalline material.

8. The method of claim 7, wherein said tallying comprises counting a number of frames with a specific type of said crystalline defect and without said specific type of crystalline defect.

9. The method of claim 1, wherein said crystalline material comprises a plurality of patterned structures present on a surface of a substrate, each patterned structure of said plurality of patterned structures is misaligned relative to the known crystallographic angles at least one type of crystalline defect present in each patterned structure.

10. A method for automatic detection of crystalline defects of a crystalline material, said method comprising:
    providing a substrate containing a plurality of patterned structures comprising a crystalline material, wherein each of said patterned structure is misaligned relative to at least one type of crystalline defect present in each patterned structure; and
    obtaining an image of each patterned structure utilizing electron channeling contrast imaging (ECCI).

11. The method of claim 10, wherein each patterned structure is a crystalline fin.

12. The method of claim 10, further comprising:
    altering the ECCI conditions to provide second images;
    distinguish crystalline defects from other features present in said second images;
    tallying the number of said crystalline defects;
    processing, using an algorithm, features of said crystalline defects in said second images to determine the defect fingerprint for each of said crystalline defects; and
    classifying the defect type of each of said crystalline defects by comparing said defect fingerprint to a library containing images of defect fingerprints of known defect types.

13. The method of claim 12, wherein said altering said ECCI conditions comprises tilting said crystalline material.

14. The method of claim 12, wherein said altering said ECCI conditions comprises tilting said crystalline material to a complementary channeling condition.

15. The method of claim 12, wherein said altering said ECCI conditions comprises changing the accelerating voltage of the electron beam, modifying the optimum channeling conditions.

16. The method of claim 12, wherein said altering said ECCI conditions comprises changing the detector configuration to collect different finds of complementary signal.

17. The method of claim 12, wherein said processing comprises generating a line profile and two-dimensional cropped images of said crystalline defect.

18. The method of claim 12, further comprising:
    tallying and storing the number of each type of crystalline defect and the total area scanned; and
    determining the number of each type of crystalline defects per unit area of said crystalline material.

19. The method of claim 18, wherein said tallying comprises counting a number of frames with a specific type of said crystalline defect and without said specific type of said crystalline defect.

* * * * *